United States Patent
Woo et al.

(10) Patent No.: US 7,897,182 B2
(45) Date of Patent: Mar. 1, 2011

(54) COMPOSITION COMPRISING BAMBOO EXTRACT AND THE COMPOUNDS ISOLATED THEREFROM SHOWING TREATING AND PREVENTING ACTIVITY FOR INFLAMMATORY AND BLOOD CIRCULATION DISEASE

(75) Inventors: Sung-Sick Woo, Seoul (KR); Tae Hyung Jo, Gyeonggi-do (KR); Dong Seon Kim, Daejeon (KR); Sun-Young Sung, Gyeonggi-do (KR); Seon-Gil Do, Chungcheongbuk-do (KR); Young Chul Lee, Daejeon (KR); Jeong Bum Nam, Daejeon (KR); Jong Ha Ryu, Daegu (KR); Kang Woo Lee, Chungcheongnam-do (KR); Hee Sun Sung, Gyeonggi-do (KR); Young Moon Heo, Jeollabuk-do (KR); Mi-Sun Oh, Chungcheongnam-do (KR); Ji Nyeo Cho, Gyeonggi-do (KR); Sookyoung Sung, Chungcheongnam-do (KR); Ju Yeon Lee, Daegu (KR); Tae Woo Kim, Ulsan (KR); Ji Sook Song, Gyeonggi-do (KR); Seoung Ho Lee, Chungcheongbuk-do (KR); Mi Ran Kim, Seoul (KR)

(73) Assignee: Unigen, Inc., Seoul (KR)

( * ) Notice: Subject to any disclaimer, the term of this patent is extended or adjusted under 35 U.S.C. 154(b) by 0 days.

(21) Appl. No.: 11/872,845

(22) Filed: Oct. 16, 2007

(65) Prior Publication Data

US 2008/0107759 A1    May 8, 2008

Related U.S. Application Data

(63) Continuation of application No. 10/522,832, filed as application No. PCT/KR2004/000708 on Mar. 27, 2004, now abandoned.

(30) Foreign Application Priority Data

Mar. 27, 2003    (KR)    ...................... 10-2003-0019229
Mar. 27, 2003    (KR)    ...................... 10-2003-0019230

(51) Int. Cl.
    *A01N 65/00*    (2009.01)
(52) U.S. Cl. .................................... 424/725
(58) Field of Classification Search ............... None
    See application file for complete search history.

(56) References Cited

U.S. PATENT DOCUMENTS

| | | | |
|---|---|---|---|
| 4,201,776 | A | 5/1980 | Naito |
| 5,098,709 | A | 3/1992 | Kang |
| 2002/0146467 | A1 | 10/2002 | Jung et al. |
| 2004/0185124 | A1 | 9/2004 | Hayashi |
| 2008/0214658 | A1 | 9/2008 | Woo et al. |
| 2008/0279969 | A1 | 11/2008 | Jo et al. |
| 2009/0304830 | A1 | 12/2009 | Jo et al. |

FOREIGN PATENT DOCUMENTS

| | | |
|---|---|---|
| CN | 1228968 | 9/1999 |
| JP | 57038721 | 3/1982 |
| JP | 403251518 | 11/1991 |
| JP | 2001-187744 | 3/1992 |
| JP | 09-094081 | 4/1997 |
| JP | 409278662 | 10/1997 |
| JP | 2000317463 | 11/2000 |
| KR | 100465113 | 12/2004 |

OTHER PUBLICATIONS

Albrecht et al. (2002) *Am. J. Transplantation* 2:448-453.
Andriambeloson et al. (1998) *J. Nut.* 128(12):2324-2333.
Clancy et al. (2000) *J. Immunol.* 165:1582-1587.
Dinerman et al. (Aug. 1993) *Circulation. Research* 73:217-222.
Dijkstra et al. (2002) *Scand. J Gastroenterol* 37(5):546-554.
Fernandez et al. (1998) *J. Pharm Pharmacol.* 50:1183-1186.
Gobert et al. (2002) *J. Immunol.* 168(12):6002-6006.
Hu et al. (2000) *J. Agric. Food Chem.* 48:3170-3176.
Lee et al. (Sep.-Oct. 1981) *J Nat Prod.* 44:530-535.
Lo et al. (2002) *Carcinogenesis* 23(6):983-991.
Otani et al. (1990) *Int. J. Tiss. Reac.* XII(6):319-332.
Ramachandran et al. (2002) *Free Radical Biol. Med.* 33(11):1465-1474.
Sadowska-Krowicka et al. (1998) *Proc. Soc. Exp. Biol. Med.* 217(3):351-357.

(Continued)

*Primary Examiner* — Michael V Meller
(74) *Attorney, Agent, or Firm* — Swanson & Bratschun, L.L.C.

(57) ABSTRACT

The present invention relates to a composition comprising a bamboo plant extract for the prevention and treatment of inflammatory or blood circulation disease. The extracts of bamboo plant has potent anti-inflammatory activity by inhibiting NO production and blood circulation-improving activity by inhibiting elastase activity and healing the wound of vascular endothelial cell, activating u-PA expression and inhibiting PAI-1 expression, lowering cholesterol deposit and inhibiting neointima formation, therefore it can be used as a therapeutic or health care food for treating and preventing inflammatory or blood circulation diseases.

6 Claims, 9 Drawing Sheets

OTHER PUBLICATIONS

Salvemini et al. (Aug. 1993) *Proc. Nat'l. Acad. Sci. USA* 90:7240-7244.
Sakac and Sakac (2000) *Med. Pregl.* LIII(9-10):463-474.
Sartor et al. (2002) *Biochemical Pharmacology* 64:229-237.
Shibata et al. (1975) *Folia pharmacol japon* 71(5):481-490.
Snyder and Bredt et al. (May 1992) *Scientific American* pp. 28-35.
Zhang et al. (2002) *China Journal of Chinese Materia Medica* 27(4):254-257.
Office Action issued Mar. 12, 2007 in U.S. Appl. No. 10/522,832.
Written Opinion issued Jun. 17, 2004 PCT/KR2004/000708.
U.S. Appl. No. 12/445,159, filed Apr. 10, 2009, Woo et al.
Office Action issued Aug. 13, 2010 in U.S. Appl. No. 12/544,640.

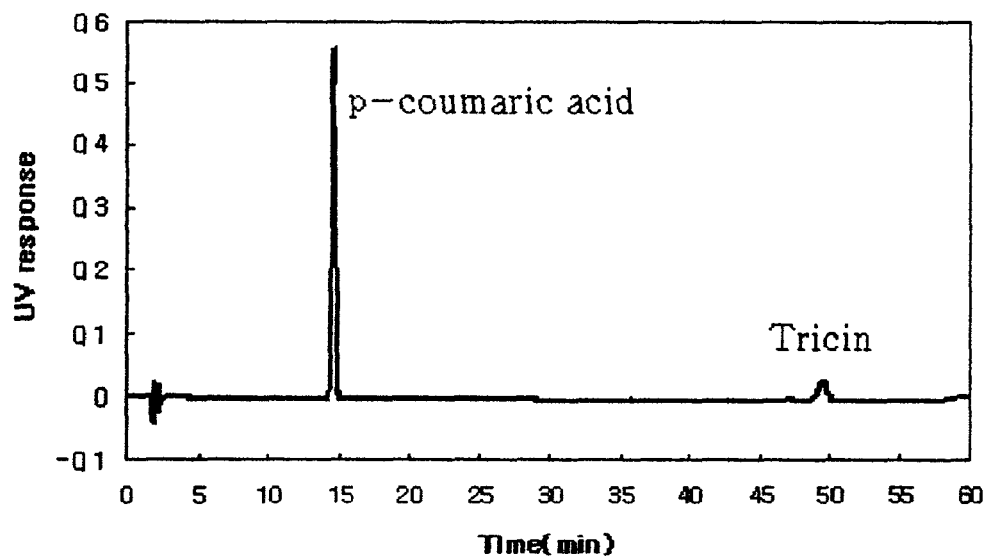
[Fig. 1]
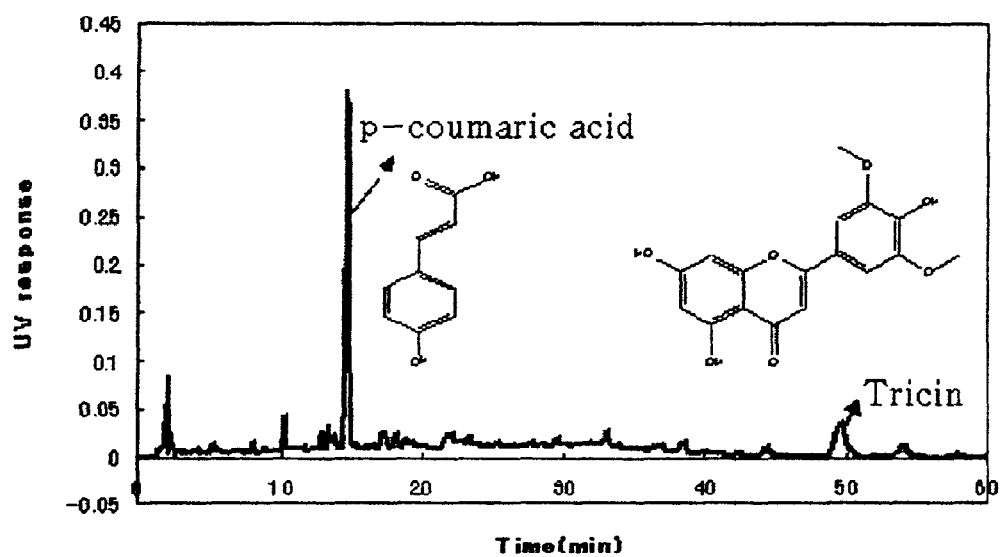
[Fig. 2]

Bamboo extract (10 μg/ml)

Bamboo extract (50 μg/ml)

COMPOSITION COMPRISING BAMBOO EXTRACT AND THE COMPOUNDS ISOLATED THEREFROM SHOWING TREATING AND PREVENTING ACTIVITY FOR INFLAMMATORY AND BLOOD CIRCULATION DISEASE

RELATED APPLICATIONS

This application is a continuation of U.S. application Ser. No. 10/522,832, filed Feb. 2, 2005, which is a 35 U.S.C. §371 national phase application of PCT/KR2004/000708 (WO 2004/098624), filed on Mar. 27, 2004, each of which is entitled "Composition Comprising Bamboo Extract and the Compounds Isolated Therefrom Showing Treating and Preventing Activity for Inflammatory and Blood Circulation Disease." PCT/KR2004/000708 (WO 2004/098624), filed on Mar. 27, 2004, claims priority to Korean Application Serial Nos. KR 10-2003-0019229 and KR 10-2003-0019230, filed Mar. 27, 2003. Each of these references is incorporated herein by reference in its entirety.

TECHNICAL FIELD

The present invention relates to banjo extract and the compound isolated therefrom showing treating and preventing activity for inflammatory and blood circulation disease.

BACKGROUND ART

Blood circulation disorder occurred by the blockage of blood flow caused by deposited cholesterol and increased thrombus on blood vessel, and lessened elastic force of blood vessel. The representative symptoms of blood circulation disorder are benumbed feet or hand, crick of neck and shoulders, loss of memory, lethargy, loss of concentration, vertigo and chronic fatigue etc., which often give difficulty in normal living life. Hyperlipemia, as one example of blood circulation disorder, is a condition where the blood lipid parameters are elevated in the blood. This condition manifests an abnormally high concentration of fats in the blood. The lipid component in the circulating blood is total cholesterol, low density lipoproteins, very low density lipoproteins or triglycerides.

Inflammation occurred by the invasion of outer contaminant, for example, bacteria, fungus, virus, various allergens inducing inflammatory response and a biophysical process against them. The characteristic syndrome of inflammatory response is serial and complex physiological response such as the enhancement of enzyme activity, the release of inflammatory mediators, fluidal infiltration, cell movement, tissue disruption together with external syndromes such as erythema, edema, pyrexia, ache and so on.

NO (nitric oxide), a factor of those inflammatory responses is formed by NOS (nitric oxide synthase), which acts on L-arginine to form final products, i.e., NO and citrulline through an intermediate (hydroxyarginine). The substance has small molecular weight and it has been found that it acts on blood vessel system to induce vasodilation, platelet agglutination and adhesion, neuronal transmission, gastrointestinal movement and plays a important roles in controlling metabolic pathway and physiological reaction such as neuronal transmission, blood coagulation, blood pressure regulation and the immunity against cancer cell etc. It is highly toxic because of its free radical structure and is prone to be changed to stabilized final product i.e., $NO_3$ and $NO_2$ in the air (Snyder S. H., et al, *Scientific American*, May pp 28-35, 1992).

NOS can be classified with cNOS (constitutive NOS) and iNOS (inducible NOS) according to the dependence to calcium ion or calmodulin; wherein cNOS dependent to calcium ion or calmodulin is present mainly in brain, epithelial cell, neutrophil, stomach mucous cell and; wherein iNOS independent to calcium ion or calmodulin is present mainly in macrophage, hepatic cell, cancer cell etc and is induced by several factors, for example, cytokines such as IL-1beta, IFN-gamma, TNF-alpha, or an endotoxin such as bacterial LPS (Dinerman, J. L., et al, *Circ. Res.*, 73, pp 217-222, 1993). iNOS expression is closely correlated with COX-2 expression, therefore, formed NO may affects on COX-2 expression (Robert C., et al., *J. Immunol.*, 165, pp 1582-1587, 2000; Daniela S., et al., *Proc. Nat'l. Acad. Sci. USA*, 90, pp 7240-7244, 1993).

Additionally, there have been many reports on the correlation between NO production caused by iNOS and various inflammatory diseases such as atheriosclerosis, arthritis, gastritis, colitis, nephritis, hepatitis, cancer or various degenerative diseases (Gobert A. P. et al., *J. Immunol.* 168(12), pp 6002-6006, 2002; Dijkstra G. et al., *Scand. J. Gastroenterol.*, 37(5) pp 546-554, 2002; Sakac V. and Sakac M. *Med. Pregl.*, 53, pp 463-474, 2000; Albrecht E. W. et al., *Am. J. Transplant*, 29(5), pp 448-453, 2002; Ramachandran A. et al., *Free Radical Biol. Med.*, 33(11) pp 1465-1474, 2002; Sartor L. et al., *Biochemical Pharmacol.*, 64, pp 229-237, 2002; Sadowska Krowicka H. et al., *Proc. Soc. Exp. Biol. Med.*, 217(3), pp 351-357 1998; Lo A. H. et al., *Carcinogenesis*, 23(6) pp 983-991, 2002)

Accordingly, there have been investigated to develop a medicine, health care food or food additives to treat and prevent above described various inflammatory diseases by finding potent inhibitors for the production of NO caused by iNOS.

Bamboo belonged to Bambusaceae or Poaceae is distributed in Asian countries including Korea and Japan. There are about 1259 species of bamboo all over the world. Among them, the representative ones belonged to Bambusaceae are *Phyllostachys bambusoides* SIEB. Et Zucc, *Phyllostachys nigra* MUNRO, *Phyllostachys nigra* MUNRO var. *henonis* STAPF and *Phyllostachys pubescens* MAZEL ex H. de LEH, and the representative ones belonged to another Poaceae are *Sasa borealis* Makino, *Sasa coreana* Nakai, *Sasa japonica* Makino, *Sasa borealis* var. *gracilis, Sasa palmata* Nakai, *Setaria viridis* BEAUV and *Oryza sativa* L.

There have been several reports on the use of bamboo extract, for example, Korean Patent Publication No. 10-2001-69130 discloses on the process for preparing the leave extract from *Sasa japonica* Makino and the use of the same as a food preservative using its antimicrobial activity; U.S. Pat. No. 3,418,311 discloses the polysaccharide isolated from bamboo having anticancer activity.

However, there has been not reported or disclosed about therapeutic effect for inflammatory or blood circulation disease of bamboo extract and the compound isolated therefrom in any of above cited literatures, the disclosures of which are incorporated herein by reference.

To investigate and confirm the treating or preventing effect on inflammatory or blood circulation disease of bamboo extract and the compound isolated therefrom through several biochemical experiments, the inventors of the present invention have intensively carried out several biological experiments i.e., in vitro inhibition test on NO or PLA2 production induced by LPS activated macrophage and an effects on the expression of several gene such as u-PA, eNOS and VEGF known to play an important role in thrombolytic activity, the control of blood flow and the cell growth in blood vessel together with cytotoxicity test, as well as animal model test using LDL receptor defected mouse and normal mouse and finally completed present invention by confirming that the extract and the compound isolated therefrom have the treating and preventing activity on inflammatory or blood circulation diseases.

These and other objects of the present invention will become apparent from the detailed disclosure of the present invention provided hereinafter.

DISCLOSURE

The present invention provides a pharmaceutical composition comprising bamboo extract or the compound isolated therefrom as an active ingredient in an effective amount to treat and prevent inflammatory disease caused by the overproduction of NO.

The present invention provides a pharmaceutical composition comprising bamboo extract or the compound isolated therefrom as an active ingredient in an effective amount to treat and prevent blood circulation disease.

The present invention also provides a use of above extract or compound for the preparation of pharmaceutical composition to treat and prevent inflammatory disease and blood circulation disease.

The present invention also provides a health care food comprising above extract or compound for the prevention or alleviation of inflammatory disease by inhibiting NO production and blood circulation disease.

Accordingly, it is an object of the present invention to provide a pharmaceutical composition comprising the crude extract, polar solvent soluble or non-polar solvent soluble extract of bamboo plant as an active ingredient for the treatment and prevention of cardiovascular disease.

It is an object of the present invention to provide a pharmaceutical composition comprising the crude extract, polar solvent soluble or non-polar solvent soluble extract of Bamboo plant as an active ingredient for the treatment and prevention of blood circulation disease by inhibiting elastase activity, healing the wound of vascular endothelial cell, activating u-PA expression, inhibiting PAI-1 expression, lowering cholesterol deposit and inhibiting neointima formation.

It is an object of the present invention to provide a pharmaceutical composition comprising the crude extract, polar solvent soluble or non-polar solvent soluble extract of bamboo plant as an active ingredient for the treatment and prevention of inflammation by inhibiting NO production and phospholipase $A_2$ expression.

The term 'crude extract' disclosed herein comprises the extract prepared by extracting plant material with water, lower alcohols such as methanol, ethanol, preferably methanol and the like, or the mixtures thereof.

The term 'polar solvent soluble extract' disclosed herein can be prepared by extracting above crude extract with polar solvent, for example, water, lower alcohol such as methanol, ethanol, preferably butanol and the like, or the mixtures thereof.

The term 'non-polar solvent soluble extract' disclosed herein can be prepared by extracting above crude extract with non-polar solvent, for example, hexane, ethyl acetate or dichloromethane, preferably ethyl acetate.

Accordingly, it is another object of the present invention to provide a pharmaceutical composition comprising tricin and p-coumaric acid isolated from bamboo plant extract as an active ingredient for the treatment and prevention of cardiovascular disease.

It is an object of the present invention to provide a pharmaceutical composition comprising tricin and p-coumaric acid isolated from bamboo plant extract as an active ingredient for the treatment and prevention of blood circulation disease by inhibiting elastase activity, healing the wound of vascular endothelial cell and increasing VEGF, u-PA and eNOS gene expression.

It is another object of the present invention to provide a pharmaceutical composition comprising tricin and p-coumaric acid isolated from bamboo plant extract as an active ingredient for the treatment and prevention of inflammation by inhibiting NO production.

The term 'bamboo plant' disclosed herein comprises the stem or leaves of bamboo plant belonged to Bambusaceae or Poraceae. Preferable plants belonged to Bambusaceae are *Phyllostachys bambusoides* SIEB. Et Zucc, *Phyllostachys nigra* MUNRO, *Phyllostachys nigra* MUNRO var. *henonis* STAPF and *Phyllostachys pubescens* MAZEL ex H. de LEH and more preferable one is *Phyllostachys nigra* MUNRO var. *henonis* STAPF. Preferable plants belonged to Poaceae are *Sasa borealis* Makino, *Sasa coreana* Nakai, *Sasa japonica* Makino, *Sasa borealis* var. *gracilis, Sasa palmata* Nakai, *Setaria viridis* BEAUV and *Oryza sativa* L and more preferable one is *Sasa borealis* Makino.

The term 'u-PA' disclosed herein is urokinase type plasminogen activator gene (fibrinolytic factor), '$PLA_2$' is phospholipase $A_2$ gene, 'VEGF' is vascular endothelial growth factor gene, 'eNOS' is endothelial nitrous oxide synthase gene and 'PAI-1' is plasminogen activator inhibitor 1 gene.

It is an object of the present invention to provide a use of a crude extract, polar solvent soluble or non-polar solvent soluble extract of bamboo plant for the preparation of therapeutic agent for the treatment and prevention of inflammatory disease by inhibiting NO production and PLA2 expression in human or mammal.

It is an object of the present invention to provide a use of a crude extract, polar solvent soluble or non-polar solvent soluble extract of bamboo plant for the preparation of therapeutic agent for treatment and prevention of blood circulation disease by inhibiting elastase activity, healing the wound of vascular endothelial cell, activating u-PA expression and inhibiting PAI-1 expression, lowering cholesterol deposit and inhibiting neointima formation in human or mammal.

It is an object of the present invention to provide a method of treating and preventing inflammatory disease by inhibiting NO production in a mammal comprising administering to said mammal an effective amount of crude extract, polar solvent soluble or non-polar solvent soluble extract of bamboo extract, together with a pharmaceutically acceptable carrier thereof.

It is an object of the present invention to provide a method of treating and preventing blood circulation disease by inhibiting elastase activity and healing the wound of vascular endothelial cell, lowering cholesterol deposit and inhibiting neointima formation in a mammal comprising administering to said mammal an effective amount of crude extract, polar solvent soluble or non-polar solvent soluble extract of bamboo extract, together with a pharmaceutically acceptable carrier thereof.

It is another object of the present invention to provide a health care food comprising above described extract or compound, together with a sitologically acceptable additive for the prevention and alleviation of inflammatory disease by inhibiting NO production and PLA expression and blood circulation disease.

The term 'cardiovascular disease' disclosed herein comprises various cardiovascular diseases such as hypertension, heart disease, brain stroke, peripheral blood disease, hyperlipemia, arteriosclerosis, stenosis, thrombosis or cardiac infarction etc.

The term 'inflammatory disease' disclosed herein comprises various inflammatory diseases such as atheriosclerosis, arthritis, gastritis, colitis, nephritis, hepatitis, cancer or various degenerative diseases.

The pharmaceutical composition of the present invention can contain about 0.1~70% by weight of the above extract or compound based on the total weight of the composition.

The health care food of the present invention comprises the above extract or compound as 0.01 to 80%, preferably 1 to 60% by weight based on the total weight of the composition.

Above health care food can be contained in health care food, health beverage etc, and may be used as powder, granule, tablet, chewing tablet, capsule, beverage etc.

An inventive extract and compound isolated from bamboo plant may be prepared in accordance with the following preferred embodiment.

Hereinafter, the present invention is described in detail.

An inventive extract of bamboo plant can be prepared in detail by following procedures, The inventive crude extract of *Phyllostachys nigra* MUNRO var. *henonis* STAPF or *Sasa borealis* Makino can be prepared by follows; *Phyllostachys nigra* MUNRO var. *henonis* STAPF or *Sasa borealis* Makino is dried, cut, crushed and mixed with 5 to 25-fold, preferably, approximately 10 fold volume of distilled water, lower alcohols such as methanol, ethanol, butanol and the like, or the mixtures thereof, preferably methanol; the solution is treated with hot water at the temperature ranging from 20 to 100° C., preferably from 60 to 100° C., for the period ranging from 1 to 24 hours with extraction method by the extraction with hot water, cold water, reflux extraction, or ultra-sonication extraction with 1 to 5 times, preferably 2 to 3 times, consecutively; the residue is filtered to obtain the supernatant to be concentrated with rotary evaporator, at the temperature ranging from 20 to 100° C., preferably from 50 to 70° C. and then dried by vacuum freeze-drying, hot air-drying or spray drying to obtain dried crude extract powder of *Phyllostachys nigra* MUNRO var. *henonis* STAPF or *Sasa borealis* Makino which can be soluble in water, lower alcohols, or the mixtures thereof.

Additionally, polar solvent soluble and non-polar solvent soluble extract of present invention can be prepared by following procedure; the crude extract prepared by above step, is suspended in water, and then is mixed with 1 to 100-fold, preferably, 1 to 5-fold volume of non polar solvent such as ethyl acetate, chloroform, hexane and the like; the non-polar solvent soluble layer is collected to obtain non-polar solvent soluble extract of the present invention and remaining polar solvent soluble layer is collected to obtain polar solvent soluble extract of the present invention which is soluble in water, lower alcohols, or the mixtures thereof. Also, above described procedures may be modified or subjected to further step to fractionate or isolate more potent fractions or compounds by conventional procedure well-known in the art, for example, the procedure disclosed in the literature (Harborne J. B. Phytochemical methods: *A guide to modern techniques of plant analysis*, $3^{rd}$ Ed. pp 6-7, 1998).

To investigate the effect of bamboo plant extract on inflammation and blood circulation through several biochemical experiments and to confirm whether the crude extract and non-polar solvent soluble extract play an important role in inhibiting NO production, main cause of inflammation, and in improving blood circulation or not, and then it is confirmed that the crude extract, polar solvent soluble and non-polar solvent soluble extract inhibit the NO production, iNOS gene expression, elastase activity and PAI-1 gene expression, promotes the u-PA gene expression and shows in vitro wound healing, in vitro tube formation activity and inhibit cholesterol deposit and neointima formation.

In accordance with another aspect of the present invention, there is provided a pharmaceutical composition comprising the crude extract, polar solvent soluble or non-polar solvent soluble extract of *Phyllostachys nigra* MUNRO var. *henonis* STAPF or *Sasa borealis* Makino prepared by above preparation method for the treatment and prevention of inflammation by inhibiting NO production as active ingredients.

It is another of the present invention to provide a treating method and preventing method comprising administering a pharmaceutical composition comprising said extract prepared by above preparation method to said mammals including human for treating inflammation or blood circulation disease.

The inventive composition for treating and preventing inflammation by inhibiting NO production and for improving blood circulation may comprises above extracts as 0.1~70% by weight based on the total weight of the composition.

The inventive composition may additionally comprise conventional carrier, adjuvants or diluents in accordance with a using method well known in the art. It is preferable that said carrier is used as appropriate substance according to the usage and application method, but it is not limited. Appropriate diluents are listed in the written text of Remington's Pharmaceutical Science (Mack Publishing co, Easton Pa.).

Hereinafter, the following formulation methods and excipients are merely exemplary and in no way limit the invention.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate or mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents that are commonly used to produce an injection. Suitable examples of the carriers include physiological saline, polyethylene glycol, ethanol, vegetable oils, isopropyl myristate, etc., but are not limited to them. For topical administration, the extract of the present invention can be formulated in the form of ointments and creams.

Pharmaceutical formulations containing present composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

The composition of the present invention in pharmaceutical dosage forms may be used in the form of their pharmaceutically acceptable salts, and also may be used alone or in appropriate association, as well as in combination with other pharmaceutically active compounds.

The desirable dose of the inventive extract or compound varies depending on the condition and the weight of the subject, severity, drug form, route and a period of administration, and may be chosen by those skilled in the art. However, in order to obtain desirable effects, it is generally recommended to administer at the amount ranging 10 g/kg, preferably, 1 to 3 g/kg by weight/day of the inventive extract or compounds of the present invention. The dose may be administered in single or divided into several times per day. In terms of composition, the amount of inventive extract should be present between 0.01 to 70% by weight, preferably 0.5 to 50% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

The term 'health care food' disclosed herein comprises dietary supplement, nutraceuticals, food or food additives.

Also, the present invention provide a composition of the health care food beverage for the prevention or improvement of inflammation or blood circulation adding above described extracts 0.01 to 80% by weight, amino acids 0.001 to 5% by weight, vitamins 0.001 to 2% by weight, sugars 0.001 to 20% by weight, organic acids 0.001 to 10% by weight, sweetener and flavors of proper amount.

Above described extract of bamboo plant can be added to food and beverage for the prevention and improvement of inflammation or blood circulation.

To develop for health care food, examples of addable food comprising above extracts of the present invention are various food, beverage, gum, vitamin complex, health improving food and the like, and can be used as power, granule, tablet, chewing tablet, capsule or beverage etc.

Also, the extract of the present invention will be able to prevent and improve allergic disease and non-allergic inflammation disease by adding to child and infant food, such as modified milk powder, modified milk powder for a growth period, modified food for a growth period.

Above described composition therein can be added to food, additive or beverage, wherein the amount of above described extract in food or beverage may generally range from about 0.1 to 80 w/w %, preferably 1 to 50 w/w % of total weight of food for the health care food composition and 1 to 30 g, preferably 3 to 10 g on the ratio of 100 ml of the health beverage composition.

Providing that the health beverage composition of present invention contains above described extract as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 ml of present beverage composition.

The other components than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition. Examples of addable food comprising aforementioned extract therein are various food, beverage, gum, vitamin complex, health improving food and the like.

The inventive composition may additionally comprise one or more than one of organic acid, such as citric acid, fumaric acid, adipic acid, lactic acid, malic acid; phosphate, such as phosphate, sodium phosphate, potassium phosphate, acid pyrophosphate, polyphosphate; natural anti-oxidants, such as polyphenol, catechin, alpha-tocopherol, rosemary extract, vitamin C, green tea extract, licorice root extract, chitosan, tannic acid, phytic acid etc.

The above extract of bamboo plant may be 20 to 90% high concentrated liquid, power, or granule type.

Similarly, the above extract of bamboo plant can comprise additionally one or more than one of lactose, casein, dextrose, glucose, sucrose and sorbitol.

Inventive extract of the present invention have no toxicity and adverse effect therefore; they can be used with safe.

It will be apparent to those skilled in the art that various modifications and variations can be made in the compositions, use and preparations of the present invention without departing from the spirit or scope of the invention.

DESCRIPTION OF DRAWINGS

The above and other objects, features and other advantages of the present invention will more clearly understood from the following detailed description taken in conjunction with the accompanying drawings, in which;

FIGS. 1 and 2 represent the HPLC analysis data of tricin and p-coumaric acid, FIG. 1 is for standard group, FIG. 2 is for inventive bamboo extract;

FIG. 3 is for 50 μg/ml treated group, FIG. 4 is for 100 μg/ml treated group, wherein A: crude extract, B: n-hexane soluble extract, C: dichloromethane soluble extract, D: n-butanol soluble extract, E: ethyl-acetate soluble extract, F: water-soluble extract;

FIG. 7 is for VEGF expression, FIG. 8 is for u-PA expression and FIG. 9 is for eNOS expression, wherein the numbers described above the graph bars denote the concentration of treated sample (μg/ml);

FIG. 10 is for control group, FIG. 11 is for 10

μg/ml bamboo extract-treated group and FIG. 12 is for 50 μg/ml of bamboo extract-treated group;

FIG. 13 is for control group, FIG. 14 is for 10 μg/ml of bamboo extract-treated group and FIG. 15 is for 100 μg/ml of bamboo extract-treated group;

FIG. 17 represents Oil red O stained photographs of frozen sections of aortic valve lesion, wherein the left panel is for control group, the middle panel is for positive control group treated with Lovastatin and right panel is for bamboo extract-treated group, and FIG. 18 represents morphometric results of aortic valve lesion areas by computer-associated image analysis.

BEST MODE

Figure 3:
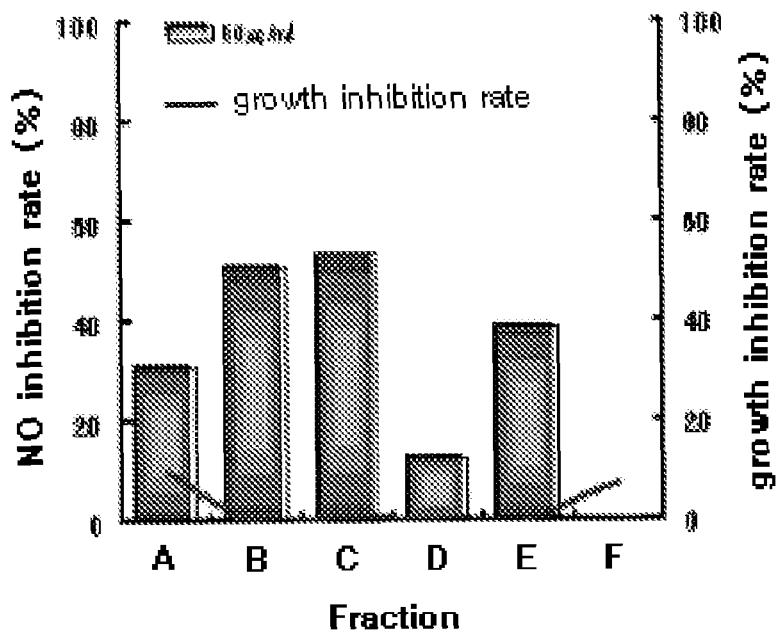
FIGS. 3 and 4 show the effects of various concentrations of bamboo crude extract and fractions isolated therefrom on NO inhibition.

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

The following Reference Example, Examples and Experimental Examples are intended to further illustrate the present invention without limiting its scope.

Example 1

Preparation of the Crude Extract of Bamboo Plant

Bamboo plants of *Sasa borealis* Makino, *Sasa coreana* Nakai, *Sasa japonica* Makino, *Sasa borealis* var. *gracilis*, *Sasa palmata* Nakai, *Phyllostachys nigra* MUNRO var. *henonis* STAPF, *Phyllostachys bambusoides* SIEB. Et Zucc., *Phyllostachys nigra* MUNRO, and *Phyllostachys pubescens* MAZEL ex H. de LEH were washed, dried for 10 days at room temperature.

10 kg of dried leaves or stem of bamboo plant were cut into small pieces, mixed with 100 L of 70% ethanol and the mixture was heated 3 times at 80° C. for 7 hours, repeatedly. And the extract was filtered with filter paper (Whatman Co., U.S.A.). The filtrates were pooled and concentrated by rotary evaporator (N-1000, Eyela Co. Japan) at 55~65° C. under reduced pressure and dried with freezing dryer (Speed Spec 3000, Bio-Rad, U.S.A.) to obtain dried crude extract of each bamboo plant (See Table 1).

TABLE 1

|  | Leaf | Stem |
|---|---|---|
| *Sasa borealis* Makino | 880 g | 880 g |
| *Sasa coreana* Nakai | 850 g | 640 g |
| *Sasa japonica* Makino | 750 g | 550 g |
| *Sasa borealis* var. *gracilis* | 810 g | 760 g |
| *Sasa palmata* Nakai | 9070 g | 790 g |
| *Phyllostachys nigra* MUNRO var. *henonis* STAPF | 810 g | 740 g |
| *Phyllostachys bambusoides* SIEB. EtZucc. | 1030 g | 870 g |
| *Phyllostachys nigra* MUNRO | 840 g | 870 g |
| *Phyllostachys pubescens* MAZEL ex H. de LEH | 1160 g | 840 g |

Example 2

Preparation of Polar Solvent and Non-Polar Solvent Soluble Extract of *Phyllostachys nigra*

2-1. Preparation of n-Hexane Soluble Extract 50 g of crude extract of *Phyllostachys nigra* prepared in Example 1 was suspended in 1 liter of distilled water and the suspension was mixed with 1 liter of n-hexane vigorously to divide into n-hexane soluble fraction and water-soluble fraction. n-hexane soluble fraction was collected and the residual solution was subjected to the n-hexane extraction again. Above-described procedure was repeated 3 times.

n-hexane soluble fraction was evaporated in vacuo to give 9.1 g of n-hexane soluble extract of *Phyllostachys nigra*.

2-2. Preparation of Dichloromethane Soluble Extract

Water-soluble fraction of *Phyllostachys nigra* prepared in Example 2-1 was mixed with equivalent volume of dichloromethane vigorously to divide into dichloromethane soluble fraction and water-soluble fraction. Dichloromethane soluble fraction was collected and the residual solution was subjected to the dichloromethane extraction again. Above-described procedure was repeated 3 times.

Dichloromethane soluble fraction was evaporated in vacuo to give 4.6 g of dichloromethane soluble extract of *Phyllostachys nigra*.

2-3. Preparation of Ethylacetate Soluble Extract

Water-soluble fraction of *Phyllostachys nigra* in Example 2-2 was mixed with equivalent volume of ethylacetate vigorously to divide into ethylacetate soluble fraction and water-soluble fraction. Ethylacetate soluble fraction was collected and the residual solution was subjected to the ethylacetate extraction again. Above-described procedure was repeated 3 times.

Ethyl acetate soluble fraction was evaporated in vacuo to give 4.3 g of ethylacetate soluble extract of *Phyllostachys nigra*.

2-4. Preparation of n-butanol and Water-Soluble Extract

Water-soluble fraction of *Phyllostachys nigra* in Example 2-3 was mixed with equivalent volume of n-butanol vigorously to divide into n-butanol soluble fraction and water-soluble fraction. n-butanol soluble fraction was collected and the residual solution was subjected to the n-butanol extraction again. Above-described procedure was repeated 3 times.

n-butanol soluble fraction and water-soluble fraction were respectively evaporated in vacuo to give 7.1 g of n-butanol soluble extract and 25.1 g of water-soluble extract of *Phyllostachys nigra*.

Example 3

Preparation of Polar Solvent and Non-Polar Solvent Soluble Extract of *Sasa borealis* (1)

As shown in the Table 2, each polar solvent and non-polar solvent soluble extract was prepared according to the identical method disclosed in the above Example 2.

TABLE 2

|  | Amount |
| --- | --- |
| Crude extract | 57 g |
| n-hexane soluble extract | 9.5 g |
| Dichloromethane soluble extract | 4.1 g |
| Ethyl acetate soluble extract | 4.8 g |
| n-butanol soluble extract | 27.9 g |
| Water-soluble extract | 27.9 g |

Example 4

Preparation of Polar Solvent and Non-Polar Solvent Soluble Extract of *Sasa borealis* (2)

The dried extract from the stem of *Sasa borealis* Makino prepared in Example 1 was subject to fractionation as follows.

100 g of the crude extract obtained in Example 1 was suspended in 1000 ml of distilled water. 1000 ml of chloroform was added thereto in separatory funnel and the mixture was shaken vigorously to divide into chloroform soluble layer and water soluble layer. Chloroform soluble fraction was collected and the residual solution was subjected to the chloroform extraction again.

Above-described procedure was repeated 3 times to separate the chloroform soluble component and chloroform soluble fraction was collected and dried under reduced pressure to obtain 17.8 g of chloroform soluble fraction.

Above water soluble fraction was mixed with equivalent amount of ethyl acetate and then divided into ethyl acetate soluble layer and water-soluble layer. The fractionation process was repeated 3 times.

Above ethyl acetate soluble layer was concentrated by rotary evaporator, dried under reduced pressure to obtain 15.4 g of ethyl acetate soluble extract.

Finally, water-soluble layer was also obtained to use as a sample in the following experiments.

Example 5

Isolation of Tricin and p-coumaric Acid 10 g of ethyl acetate soluble fraction prepared in Example 4 was subjected to Silica gel column chromatography to isolate tricin and p-coumaric acid.

10 g of ethyl acetate fraction was loaded onto the Silica gel column and the column was eluted with a stepwise application of solvent mixture containing linear gradient of chloroform:acetone (100:1→1:1) to give 7 sub-fractions. Among 7 fractions, the 4th fraction was recrystallized using methanol and 26 mg of yellow crystal was isolated therefrom.

Above prepared yellow crystal was subjected to thin layer chromatography using TLC plate (Silica gel 60 F254 plate, layer thickness 0.2 mm, 20×20, Merck Co, Germany) and chloroform:methanol (20:1) mixture as a developing solvent. The TLC result showed that the crystal was detected as a yellow spot in anisaldehyde-$H_2SO_4$ treatment and as a dark brown spot in 365 nm UV light (Power wave-XS, Bio-Tek, USA) with 0.4 of $R_f$ (solvent system: ($CHCl_3$:MeOH=20:1).

And the result of $^1H$ and $^{13}C$-NMR data by NMR spectroscopy ($^1H$: 300 MHz, $^{13}C$: 75 MHz, DRX 300, Bruker, Germany) showed that the yellow crystal was identified as a tricin and the spectral data were shown as below.

Tricin: $C_{17}H_{14}O_7$ $^1H$-NMR (300 MHz, d6-DMSO): delta 12.96 (5-OH, 1H, s), 7.33 (H-2', H-6', 2H, s), 6.97 (H-3, 1H, s), 6.56 (H-8, 1H, d, J=2.0 Hz), 6.21 (H-6, 1H, d, J=2.0 Hz), 3.89 (—$OCH_3$, 6H, s).

$^{13}C$-NMR (75 MHz, d6-DMSO): delta 182.66 (C-4), 164.96 (C-2), 164.53 (C-7), 162.26 (C-5), 158.21 (C-9), 149.07 (C-3', 5'), 140.74 (C-4'), 121.30 (C-1'), 105.32 (C-3), 104.61 (C-2', 6'), 104.46 (C-10), 99.69 (C-6), 95.04 (C-8), 57.26 (—$OCH_3$)

Among 7 fractions, the $7^{th}$ fraction was subjected to preparation HPLC to obtain 4.2 mg of phenyl propanoid compound and the isolated phenylpropanoid compound was identified as p-coumaric acid derivatives by the result of $^1H$-NMR spectrum by NMR spectroscopy ($^1H$: 300 MHz, DRX 300, Bruker, Germany) shown as below and the retention time of HPLC analysis compared with the data of p-coumaric acid standard purchased from Sigma Company (See FIGS. 1 and 2).

p-Coumaric acid: $C_9H_8O_3$ $^1H$-NMR (300 MHz, d6-DMSO): δ 7.5 (H-2, H-6, 2H, d., J=8.4 Hz), 7.48 (H-gamma, 1H, d., J=16.2 Hz, 6.79 (H-3, H-5, 2H, d., J=8.4 Hz), 6.285 (H-beta, 1H, d., J=16.2 Hz).

Example 6

Content Analysis of Tricin and p-coumaric Acid

Each 10 g of stem extract and leaf extract of *Sasa borealis* Makino, *Sasa coreana* Nakai, *Sasa japonica* Makino, *Sasa borealis* var. *gracilis, Sasa palmata* Nakai, *Phyllostachys nigra* MUNRO var. *henonis* STAPF, *Phyllostachys bambusoides* SIEB. Et Zucc., *Phyllostachys nigra* MUNRO or *Phyllostachys pubescens* MAZEL ex H. de LEH was used to analyze the content of tricin and p-coumaric acid in the different part of plant by HPLC (Hitachi Co. L-7000 model). HPLC analysis was performed on condition shown in Table 3.

TABLE 3

| Time (min) | A* | B** | C*** |
| --- | --- | --- | --- |
| 0 | 100 | 0 | 0 |
| 30 | 0 | 100 | 0 |
| 60 | 0 | 100 | 0 |
| 65 | 0 | 0 | 100 |
| 75 | 0 | 0 | 100 |
| 80 | 100 | 0 | 0 |
| 85 | 100 | 0 | 0 |

A* solution: 0.1% $H_3PO_4$ in ACN:$H_2O$(1:9)
B** solution: 0.1% $H_3PO_4$ in ACN:$H_2O$(25:75)
C*** solution 100% CAN
Condition: Stationary phase(phenomenex C18, 4.6 × 250 mm, 5 μm) at 35° C., the wavelength at the detectors(330 nm), 10 μl of samples were injected by 50000 ppm.

The content of tricin and p-coumaric acid in various bamboo leaf extract and bamboo stem extract was shown in Table 4 and Table 5 respectively.

TABLE 4

|  | Leaf (70% ethanol extract) | |
| --- | --- | --- |
|  | tricin | p-coumaric acid |
| Sasa borealis Makino | 13 mg | 26 mg |
| Sasa coreana Nakai | 15 mg | 34 mg |
| Sasa japonica Makino | 14 mg | 5 mg |
| Sasa borealis var. gracilis | 5 mg | 7 mg |
| Sasa palmata Nakai | 3 mg | 1.3 mg |
| Phyllostachys nigra MUNRO var. henonis STAPF | 18 mg | 34 mg |
| Phyllostachys bambusoides SIEB. Et Zucc. | 5 mg | 1.5 mg |
| Phyllostachys nigra MUNRO | 5 mg | 39 mg |
| Phyllostachys pubescens MAZEL ex H. de LEH | 3 mg | 2.1 mg |

TABLE 5

|  | Stem (70% ethanol extract) | |
| --- | --- | --- |
|  | tricin | p-coumaric acid |
| Sasa borealis Makino | 18 mg | 52 mg |
| Sasa coreana Nakai | 28 mg | 83 mg |
| Sasa japonica Makino | 23 mg | 16 mg |
| Sasa borealis var. gracilis | 7 mg | 17 mg |
| Sasa palmata Nakai | 5 mg | 11 mg |
| Phyllostachys nigra MUNRO var. henonis STAPF | 26 mg | 33 mg |
| Phyllostachys bambusoides SIEB.Et Zucc. | 12 mg | 32 mg |
| Phyllostachys nigra MUNRO | 13 mg | 58 mg |
| Phyllostachys pubescens MAZEL ex H. de LEH | 23 mg | 41 mg |

Reference Example 1

Cell Culture and Reagent 1-1 Cell Culture

Murine macrophage cell line RAW 264.7 cell (ATCC, Rockville, Md., USA) were grown in DMEM (Gibco BRL Co., Ltd., USA), supplemented with 2.0 mM L-arginine, 100 µg/ml penicillin-streptomycin and 10% fetal bovine serum at 37° C. in 5% $CO_2$ and 95% air condition in humidified incubator.

Medium was changed with 10 ml fresh DMEM 4 times per week and cells were passaged 2 times per week.

HUVEC (Human umbilical vein endothelial cell) was cultured on 0.2% gelatin coating flask (MTT Co.) in the EGM-2 media (Clonetics Co.) supplemented with 20% FBS, 100× antibiotics and 200×ECGF and the cells passaged 3 to 5 times were used in the following experiment.

1-2 Reagent and Instrument

Centrifuge (Hanil Centrifuge Co. Ltd, Korea), NMR Spectroscopy ($^1$H; 300 MHz, $^{13}$C; 75 MHz, DRX 300, Bruker Germany) and UV Spectroscopy (Power wave-XS model, Bio-Tek Co. Ltd, USA) were used in Korea Basic Science Institute located in Korea, Silica gel 60H (230-400 mesh, Merck, Germany) was used as a column chromatographic absorbent and Silica gel 60 F254 Plate (layer thickness 0.2 mm, 20×20 cm, Art. 5554, Merck, Germany) was used as a TLC plate. Anisaldehyde-sulfuric acid reagent was used as a developer and all the organic solvent were purchased from Duksan Chemical. Co. Ltd. in Korea.

Experimental Example 1

Animal Model Test 1-1. Experimental Animal

To evaluate the efficacy of bamboo extract on the protection of blood vessel and the improvement of blood circulation, arteriosclerosis model mice were used in the experiment.

Six-weeks old male LDL receptor defected mouse (B6. 129S7-Ldlrtm1Her) procured from Jackson Co. Ltd. (USA) had been acclimated to the experimental environment from 1 week ago by administrating the increasing ratio of fatty feed, i.e., ratio of normal feed to high fat feed was gradually increased (7:3 at 2nd day, 5:5 at 4th day, 3:7 at 6th day). During the experiment, the environment of the cage was maintained to the temperature of 23±2° C. and the relative humidity of 55±10° C. under the artificial lamp for 12 hours, and less than five mice were bred in each mouse cage providing with free access to water (disinfected distilled water) and normal fatty feed (Harlan 2018S, Indianapolis USA). After 8 weeks, only high fat feed (Harlan TD88051, Artherosclerotic diet, overall fat content is about 15.8%; cholesterol level of 1.25%, and sodium cholate at 0.5%, about 4 kcal/g, and 35% of kcal from fat. About half the fat come from added cocoa butter, and half from the chow) were provided.

1-2. Grouping and Administration Period

Eight-weeks old male LDL receptor defected mouse accumulated to high fat feed were divided into two dose administration groups and one high dosing group of which group consist of six mice per group, Injectable distilled water was used as a negative control group, lovastain well known to be as an atheriosclerosis treating agent was administrated in an amount of 4 mg/kg per body weight as a positive control group, Bamboo was administrated to two treatment group in an amount of 50 and 100 mg/kg per body weight respectively, and one high dosing treatment group in an amount of 500 mg/kg per body weight for 20 weeks by way of compulsory oral administration after weighing the body weight twice a day (See Table 6).

TABLE 6

| The experimental groups | | |
| --- | --- | --- |
| Groups | Diets | Animal No. |
| Control | High fat diet | 6 |
| Positive control | High fat diet plus lovastatin 4 mg/kg | 6 |
| bamboo-50 | High fat diet plus sample dose 50 mg/kg | 6 |
| bamboo-100 | High fat diet plus sample dose 100 mg/kg | 6 |
| bamboo-500 | High fat diet plus sample dose 500 mg/kg | 6 |

1-3. Experimental Animal

To evaluate the efficacy of bamboo extract on the protection of blood vessel and the improvement of blood circulation, atherosclerosis model mice were used in the experiment.

Six-weeks old male C57BL/J6 mouse procured from Jackson Co. Ltd. (USA) had been acclimated to the experimental environment from 1 week ago by administrating the increasing ratio of fatty feed, i.e., ratio of normal feed to high fat feed was gradually increased (7:3 at 2nd day, 5:5 at 4th day, 3:7 at 6th day). During the experiment, the environment of the cage was maintained to the temperature of 23±2° C. and the relative humidity of 55±10° C. under the artificial lamp for 12 hours, and less than five mice were bred in each mouse cage providing with free access to water (disinfected distilled water) and normal fatty feed (Harlan 2018S, Indianapolis USA). After 8 weeks, only high fat feed (Harlan TD88051, Atherosclerotic diet, overall fat content is about 15.8%; cholesterol level of 1.25%, and sodium cholate at 0.5%, about 4 kcal/g, and 35% of kcal from fat. About half the fat come from added cocoa butter, and half from the chow) were provided.

1-4. Grouping and Administration Period

Eight-weeks old male C57BL/J6 mouse accumulated to high fat feed were divided into two dose administration consist of six mice per group, Injectable distilled water was used as a negative control group, bamboo was administrated to two treatment group in an amount of 50 and 100 mg/kg per body weight for 6 months by way of compulsory oral administration after weighing the body weight twice a day (See Table 7).

TABLE 7

The experimental groups

| Groups | Diets | Animal No. |
|---|---|---|
| Control | High fat diet | 6 |
| bamboo-50 | High fat diet plus sample dose 50 mg/kg | 6 |
| bamboo-100 | High fat diet plus sample dose 100 mg/kg | 6 |

Experimental Example 2

Effect of Bamboo Extract and the Compound Isolated Therefrom on NO Production

To test the inhibiting activity of bamboo extract and the compound isolated therefrom on nitric oxide (NO), which is one of inflammatory factors, the increase of NO was determined in the cells treated with extract or compound of the present invention.

200 µl of RAW 264.7 cells (1×106 cells/ml) were seeded onto each well of 96-well microtiter plate (Nunc, Sweden) and incubated for 3 hours in DMEM media containing 10% FBS. After changing media to fresh DMEM, the cells were treated with 1 µg/ml of LPS and 50 µg/ml or 100 µg/ml of bamboo extract or tricin prepared in above Example 1-5, and cultured at 37° C. for 20 hours in 5% $CO_2$ incubator.

And then 100 µl of cell supernatant of each well was transferred to new 96 well plate and 50 µl of Griess reagent (0.1% N-(1-naphtyl)ethylenediamine 2HCl, 1% sulfanilamide in 5% conc. $H_3PO_4$ in $H_2O$) was added thereto followed by incubating for 10 mins at R.T. The absorbance was measured at 540 or 550 nm using ELISA reader (Power wave-XS, Bio-Tek, USA).

Figure 4:
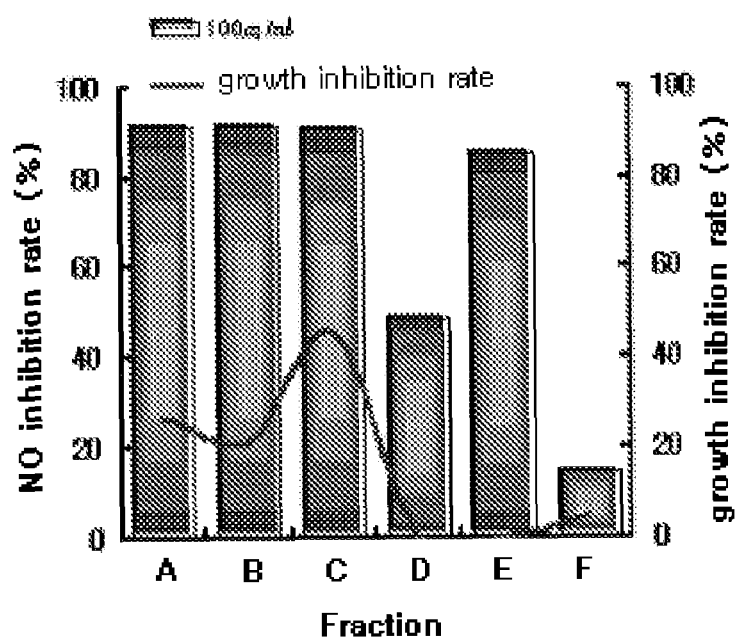

As shown in Table 8 and FIGS. 3 and 4, it was confirmed that sample treatment group with 100 and 50 µg/ml of bamboo extract inhibited NO production at the rate of 90% and 50% respectively, therefore, the bamboo extract treatment group inhibited effectively in dose dependent manner compared with control. Non-polar solvent soluble extract-treated group showed higher NO inhibition rate than polar solvent soluble extract-treated group.

TABLE 8

| | | NO inhibition rate (%) Sample | | | | | | |
|---|---|---|---|---|---|---|---|---|
| Conc. (µg/ml) | | Con | LPS treated | Crude ext. | n-hexane fr. | Dichloromethane fr. | Ethyl aceteate fr. | n-butanol fr. | Water soluble fr. |
| P. nigra | 50 | 0.34 | 0.10 | 33.1 | 51.0 | 53.6 | 39.1 | 12.5 | 0 |
| | 100 | 0.38 | 0.12 | 73.2 | 91.1 | 90.8 | 85.5 | 48.5 | 14.5 |
| S. borealis | 50 | 0.23 | 0.15 | 21.5 | 45.2 | 48.5 | 30.1 | 9.4 | 0 |
| | 100 | 0.25 | 0.14 | 60.3 | 84.3 | 82.4 | 80 | 35.1 | 9.4 |

On searching active ingredient from non-polar organic solvent, we have found that tricin prepared from Example 5 is active compound and it showed strong NO inhibition rate at the concentration of 25, 12.5 and 6.5 µg/ml of which concentration showed no toxicity (See Table 9).

TABLE 9

| Conc. of tricin (µg/ml) | NO inhibition rate (%) | Cell viability (%) |
|---|---|---|
| 50 | 49.7 ± 0.007 | 49 |
| 25 | 74.6 ± 0.009 | 80 |
| 12.5 | 71.2 ± 0.003 | 92 |
| 6.5 | 52.0 ± 0.015 | 96 |
| 3.25 | 38.1 ± 0.005 | 99 |
| 1.625 | 25.9 ± 0.006 | 126 |

Experimental Example 2

Effect of Bamboo Extract on Elastase Activity

In order to test the effect of bamboo extract on blood vessel, the inventive banjo extract was treated with elastase enzyme, which degrades elastin protein in charge of maintaining elasticity and strength of blood vessel.

Each bamboo extract or fraction prepared in Example 1-5 was diluted to 20, 2 and 0.2 mg/ml and aliquoted by 50 µg/ml into each 96 well plate. Commercial elastase (Molecula probe Co.) was added thereto at the concentration of 0.15 U/ml and elastin protein was also added at the concentration of 50 µg/ml. For determining the enzyme activity, absorbance was detected using ELISA reader.

In the result of Table 10, the inventive bamboo extract of P. nigra and S. borealis inhibited the elastase activity at 2 mg/ml and dichloromethane, ethyl acetate and n-butanol soluble fractions of bamboo extract showed more potent elastase-inhibiting activity.

TABLE 10

| | Inhibition of elastase activity (%) | | | | | |
|---|---|---|---|---|---|---|
| | Phyllostachys nigra | | | Sasa borealis | | |
| Conc. (mg/ml) | 20 | 2 | 0.2 | 20 | 2 | 0.2 |
| Control | 0 | 0 | 0 | 0 | 0 | 0 |
| Crude ext. | 92.3 | 53 | | 84.5 | 47.6 | |
| n-hexane | | 34.2 | 0 | | 21.2 | 0 |
| Dichloromethane | | 61.6 | 15.7 | | 54.6 | 15.7 |
| Ethyl acetate | | 60.8 | 33 | | 50 | 28 |
| n-butanol | | 54.6 | 7.9 | | 42 | 6.4 |
| Water soluble | | 12.1 | 1.5 | | 7.5 | 0 |

Experimental Example 3

Effect of Bamboo Extract on Wound Healing of the Endothelial Wall of the Blood Vessel 3-1. In Vivo Wound Healing Assay HUVEC was grown confluently on 0.2% gelatin-coated 12-well plate and then scratched by cell scraper to make original wound edge. The cells were treated with 10 μg/ml or 50 μg/ml of bamboo extract and cultured in 5% $CO_2$ incubator. The translocation of the cell was observed by the pictures.

Figure 10:
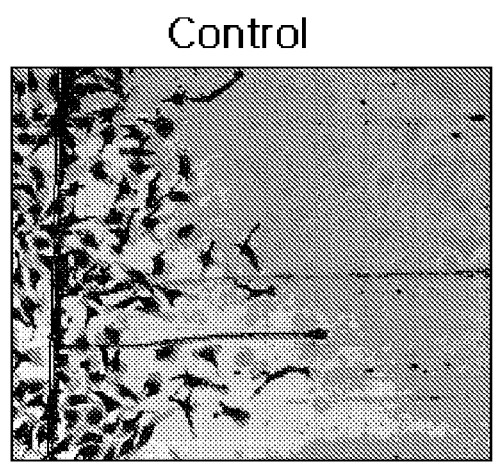
FIGS. 10 to 12 show the wound healing effect of the inventive bamboo extract through in vitro wound healing assay using HUVEC.
Figure 11:
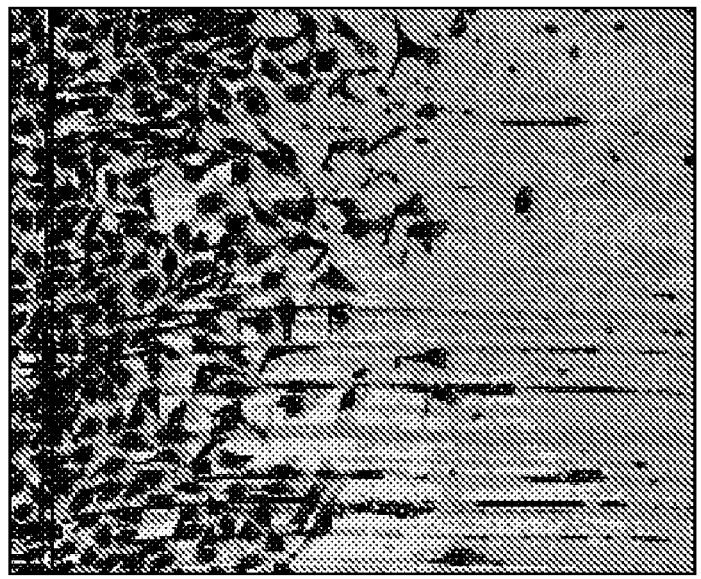
Figure 12:
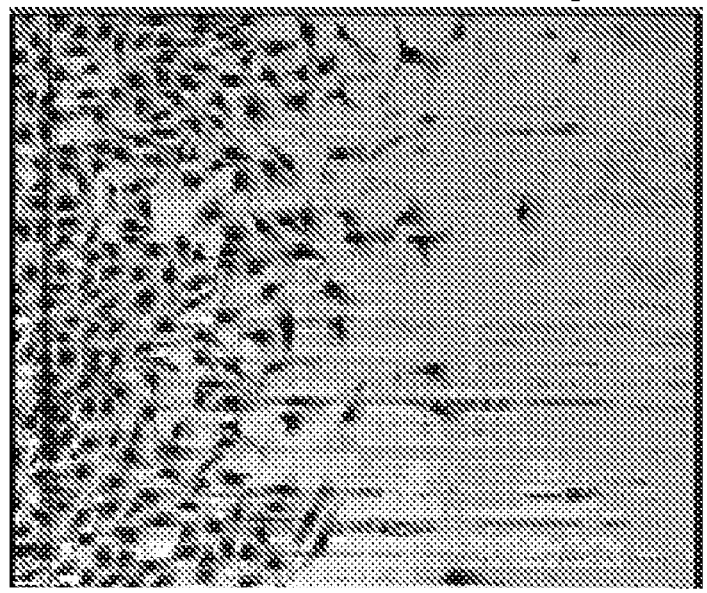

In the result of FIGS. 10 to 12, the translocation of HUVEC treated with 10-50 μg/ml of bamboo extract was apparently increased compared to that of control group, which confirmed that the bamboo extract showed the wound healing effect on the endothelial cell of blood vessel.

3-2. In Vitro Tube Formation Assay

200 μl of matrigel diluted with media (1:2) was plated on 24-well plate, incubated at 37° C. for at least 30 min to polymerize and 1000 cells/well HUVEC were seeded thereon.

The cells were treated with 10 μg/ml or 50 μg/ml of bamboo extract and cultured in 5% $CO_2$ incubator. The morphological change of the HUVEC was observed under microscope at regular interval and taken the picture.

Figure 13:
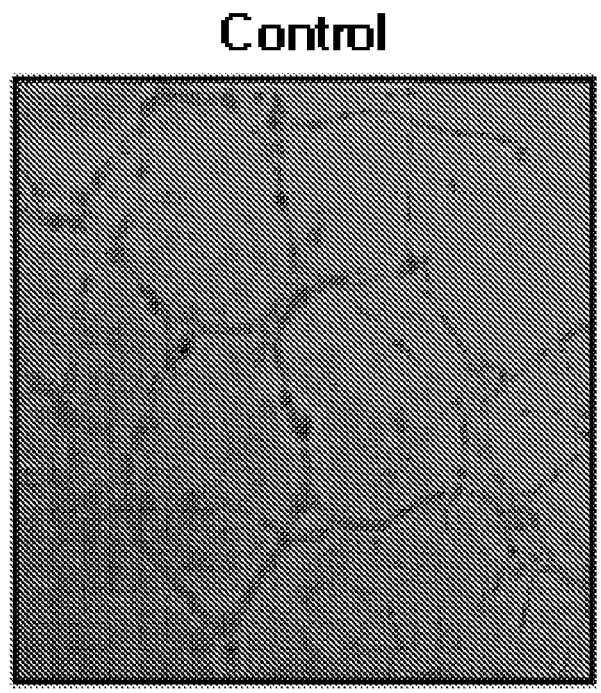
FIGS. 13 to 15 show the blood vessel formation of the inventive bamboo extract through in vitro tube formation assay using HUVEC.
Figure 14:
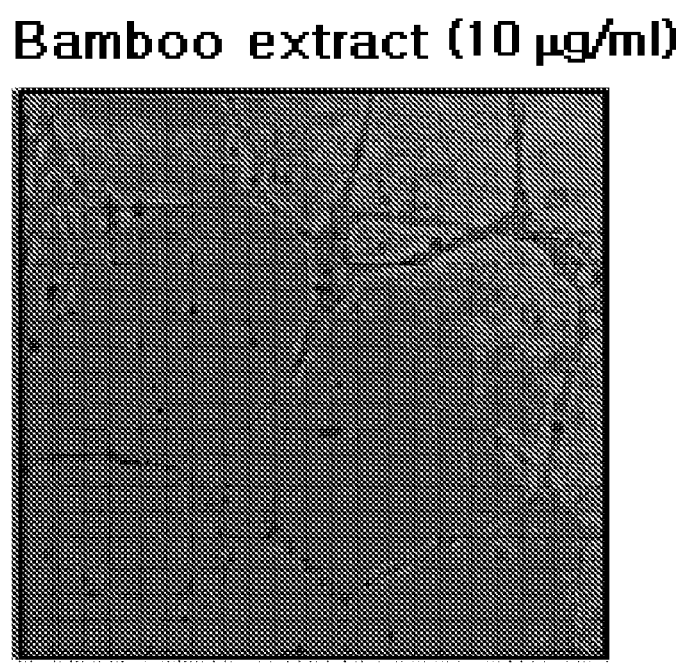
Figure 15:
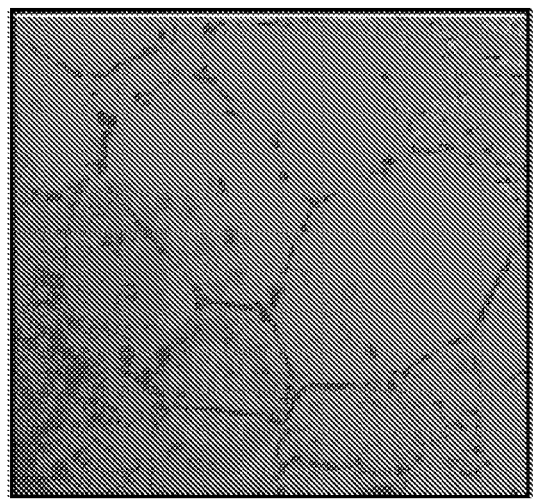

As shown in FIGS. 13 to 15, it was observed that the tube formation of HUVEC treated with 10-50 μg/ml of bamboo extract was apparently increased compared to that of control group, which confirmed that bamboo extract has the potential improving blood circulation.

As an internal control, 18S ribosomal RNA was used.

As shown in Table 11, it was known through real time-gene expression analysis that the concentrations, at which iNOS gene expression is inhibited by 90%, are 4 μg/ml for curcumin, 62.5 μg/ml for *Phyllostachys nigra* and 65 μg/ml for *Sasa borealis*.

TABLE 11

| | Inhibition of Gene expression (%) | | | |
|---|---|---|---|---|
| Conc. (μg/ml) | LPS | Curcumin | *P. nigra* | *S. borealis* |
| 0.032 | | 40% | | |
| 0.16 | | 40% | | |
| 0.625 | | | 60% | 40% |
| 0.8 | | 40% | | |
| 1.25 | | | 45% | 40% |
| 4 | 100% | 90% | | |
| 6.25 | | | 80% | 58% |
| 12.5 | | 90% | 70% | 60% |
| 25 | | | 70% | 75% |
| 62.5 | | | 90% | 85% |
| 65 | | | | 90% |

Based on the above results of Table 11, $IC_{50}$ of each sample on iNOS gene expression was calculated and presented as below Table 12.

TABLE 12

| | Comparative iNOS expression (% of control, DMSO) | | | | | | | | | | | | | | | | | $IC_{50}$ |
|---|---|---|---|---|---|---|---|---|---|---|---|---|---|---|---|---|---|---|
| | Conc. (μg/ml) | | | | | | | | | | | | | | | | | |
| Sample | 0.032 | 0.16 | 0.625 | 0.8 | 1.25 | 2.5 | 4 | 6.25 | 12.5 | 20 | 25 | 62.5 | 125 | 250 | 625 | 1250 | 2500 | (μg/ml) |
| Curcumin | 80.5 | 75.7 | | 64.4 | | | 49.9 | | | 1.3 | | | | | | | | 5.3 |
| *P. nigra* | | | 115.6 | | 125.9 | 118.5 | | 125 | 114.1 | | 49.6 | 31.6 | 27.2 | 25.4 | 23.6 | 30.2 | 25.1 | 25 |
| *S. borealis* | | | 100 | | 111 | 105 | | 92 | 87 | | 44 | 25 | 23.1 | 22 | 18 | 21 | 15 | 30 |

Experimental Example 4

Effect of Bamboo Extract and Tricin Compound on Gene Expression

To investigate the inhibiting effect on gene expression, the extract or compound of the present invention was treated to the cell and the RNA extracted therefrom was used in the RT-PCR to evaluate the quantitative gene expression.

4-1. Effect of Bamboo Extract on iNOS Gene Expression

To observe the effect of Bamboo extract on iNOS gene expression, $1\times10^6$ cells of RAW 264.7 cells were treated with LPS and various concentrations (0.032~65 μg/ml) of the inventive crude extract of *Phyllostachys nigra* or *Sasa borealis*, or curcumin and incubated for 24 hours. And RNA was extracted by conventional extraction method using Trizol reagent (Gibco BRL) to use in the following reverse transcription-polymerase chain reaction.

RT-PCR was performed according to the RT reaction (25° C. 10 min, 48° C. 30 min, 95° C. 5 min, 4° C. 10 min; 1 cycle) and subsequent PCR (50° C. 2 min, 95° C. 10 min, 95° C. 15 sec, 60° C. 1 min, 40 cycles) method well known in the art.

4-2. Effect of Bamboo Extract on PLA2 Gene Expression

To observe the effect of Bamboo extract on PLA2 enzyme, inflammatory factor related to inflammatory response, $1\times10^6$ cells of RAW 264.7 cells were treated with LPS and various concentrations (0.032~65 μg/ml) of the inventive bamboo extract and incubated for 24 hours. And RNA was extracted by conventional extraction method using Trizol reagent (Gibco BRL) to use in the following reverse transcription-polymerase chain reaction.

The OD260/OD280 value of extracted RNA determined by Spectrophotometer was more than 1.7 and the purity of RNA was confirmed by Denaturing agarose gel electrophoresis. RT-PCR was performed according to the RT reaction (10 min at 25° C., 30 min at 48° C., 5 min at 95° C., 10 min at 4° C.; 1 cycle) and subsequent PCR (2 min at 50° C., 10 min at 95° C., 15 sec at 95° C., 1 min at 60° C., 40 cycles) method well known in the art.

As an internal control, 18S ribosomal RNA was used.

As shown in Table 13, it is confirmed that bamboo extract inhibits PLA2 gene expression in a dose dependent manner compared with that of control group.

TABLE 13

| mRNA level | Control | Relative Rate | Conc. of bamboo extract (µg/ml) | | | | | | |
|---|---|---|---|---|---|---|---|---|---|
| | | | LPS | 0.625 | 1.25 | 2.5 | 6.25 | 12.5 | 25 |
| PLA2 | 1 | x | 1.8 | 1.8 | 1.8 | 1.8 | 1.5 | 1.2 | 0.9 |

4-3. Effect of Bamboo Extract on u-PA, PAI-1 Gene Expression

RNA extraction and RT-PCR were performed according to the method above described in Experimental Example 4-1.

In the result of Table 14 and 15, it was confirmed that the extracts of *Phyllostachys nigra* and *Sasa borealis* increased the expression of u-PA (urokinase type plasminogen activator) gene related to thrombolysis, while those reduced the expression of PAI-1 gene inhibiting the activity of plasminogen activator.

TABLE 14

| | u-PA (fold) | PAI-1 (fold) |
|---|---|---|
| DMSO treated control group | 1 | 1 |
| LPS | 3.65 (induction) | 4.3 (induction) |
| *P. nigra* (10 µg/ml) | 11.58 (induction) | 9.56 (inhibition) |

TABLE 15

| | u-PA (fold) | PAI-1 (fold) |
|---|---|---|
| DMSO treated control group | 1 | 1 |
| LPS | 3.81 (induction) | 4.7 (induction) |
| *S. borealis* (10 µg/ml) | 8.7 (induction) | 7.5 (inhibition) |

4-4. Effect of Tricin on VEGF, u-PA and eNOS Gene Expression

RNA was isolated from HUVEC cell by Rneasy mini kit (cat#74103, Qiagen Co.) according to the manufacturer's instruction. And RT-PCT reaction was performed by using quantitative PCR method (SDS 7700, Applied biosystems Co., U.S.A.).

5 µl of cDNA product obtained in the reverse transcription (RT) was aliquoted into each well of 96-well plate and then the mixture containing 5.6 mM $MgCl_2$, 1×PCR buffer, 2 mM dNTP, 0.05% gelatin, 1 µM of a pair of each target gene primer or 0.16 µM of house keeping gene primer, 0.5 µM of target gene probe or 0.025 µM of housekeeping gene probe, 1.25 U of Taq polymerase was added thereto for polymerase chain reaction (PCR) (50° C. 2 min, 95° C. 10 min, 95° C. 15 sec, 60° C. 1 min, 40 cycles).

As the result, final cT value was read and calculated.

Figure 7:
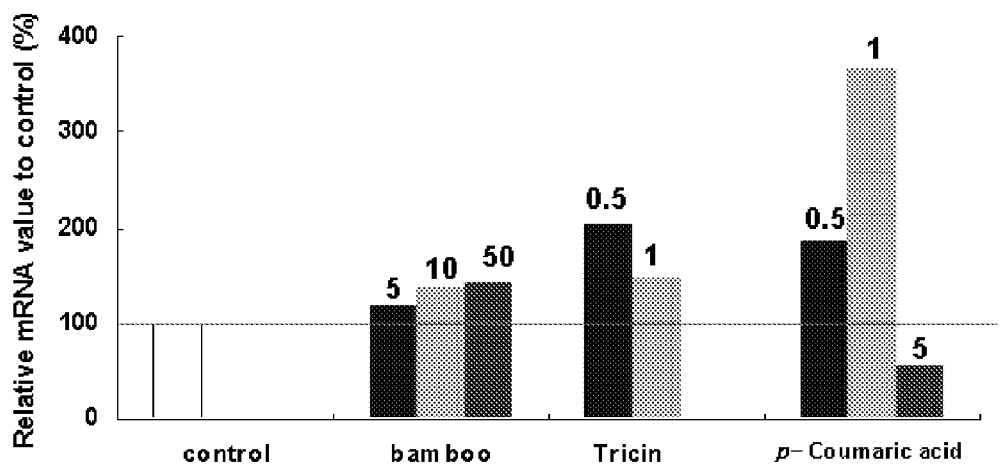
FIGS. 7 to 9 show the effect of bamboo extract, tricin and p-coumaric acid in the HUVEC with complete media on mRNA expression.
Figure 8:
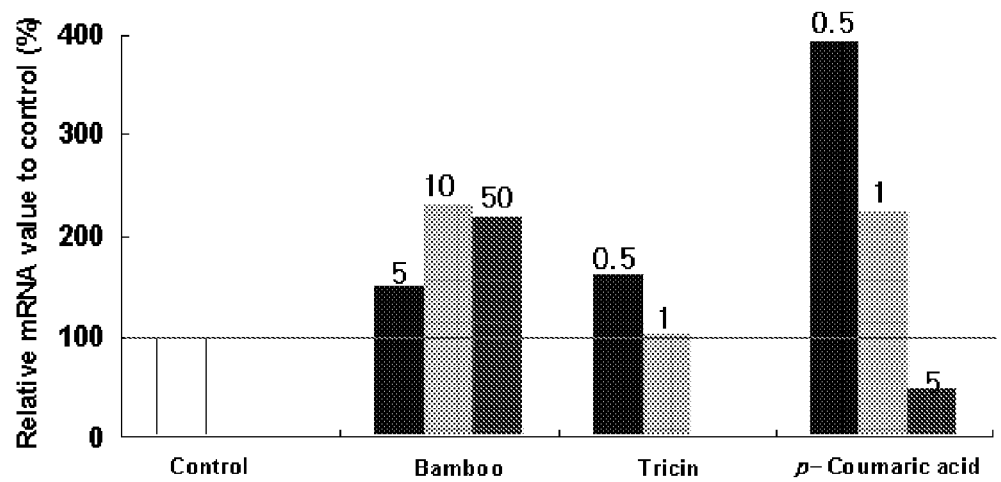
Figure 9:
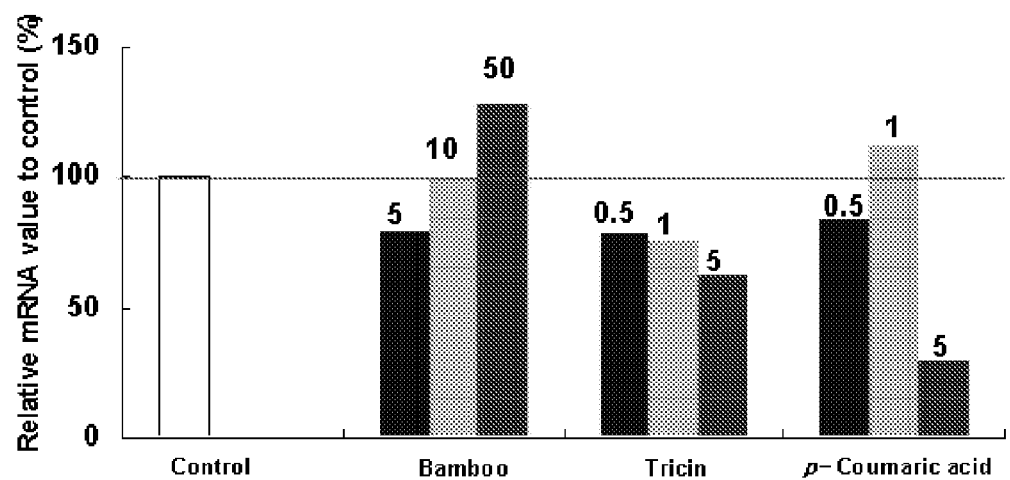

In the result of Table 16 and FIG. 7~9, tricin compound treatment to HUVEC had increased the expressions of VEGF (vascular endothelial growth factor), u-PA gene and the expression of eNOS (endothelial nitrous oxide synthase), which affects the vascular expansion in atrophy.

TABLE 16

| | | mRNA expression (fold) | | |
|---|---|---|---|---|
| Gene | Control | 0.5 µg/ml Tricin | 1.0 µg/ml Tricin | 5.0 µg/ml Tricin |
| u-PA | 1 | 1.619 | 1.103 | 2.962 |
| VEGF | 1 | 2.046 | 1.469 | 1.545 |
| eNOS | 1 | 3.024 | 4.711 | 0.452 |

Experimental Example 5

Figure 16:
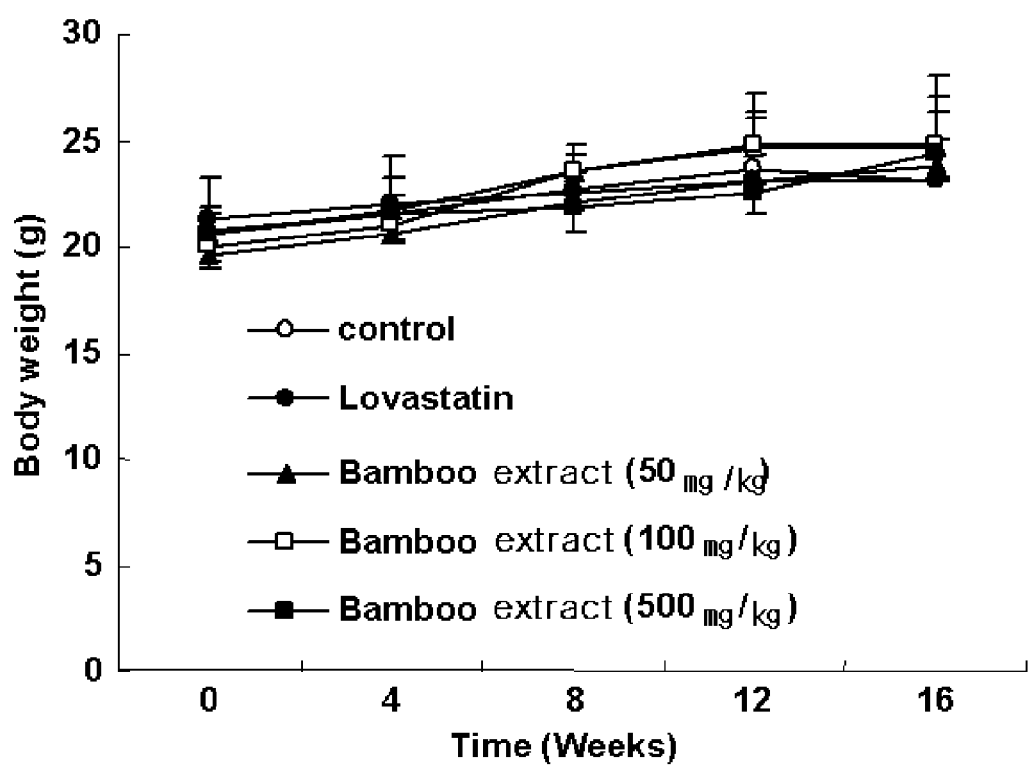
FIG. 16 shows the change of body weights in the high cholesterol diet induced atherosclerosis mice with or without the treatment of bamboo extract for 16-weeks (50 and 100 mg/kg) and 20-weeks (500 mg/kg)

Effect of Bamboo Extract on the Change of General Symptom and Body Weight in LDL Defected Mouse To investigate the effect on the change of general symptom and body weight in LDL defected mouse, the change of general symptom was observed everyday more than once a day during the treatment period and the change of body weight was determined at the time of grouping, the moment of the sample treatment and dislocation of mice after the end of experiment. At the result, we did not observed the dead mouse as well as particular clinical syndrome such as change of appearance and abnormal behavior etc (See FIG. 16). Moreover, there has been not observed in the change of body weight during the experimental period and the mean body weight of the mice was increased by about 2.00±0.6 g for each groups.

Experimental Example 6

Effect of Bamboo Extract on the Change of Blood Lipid in LDL Defected Mouse

To investigate the effect of bamboo extract on the change of blood lipid in LDL defected mouse, following method was performed.

At the end of experiment, all the mice were anesthetized with 0.12% of avertin and exsanguinations was performed from infraorbitalis plexus venosus with heparin treated capillary. And then blood plasma was isolated by centrifugation at the speed of 11,000 g for 10 minutes and left alone at −70° C. before use. The value of blood lipid was determined by three categories i.e., TC (Total cholesterol), HDL-C (High-density lipoprotein cholesterol) and TG (Triglycerides) at KRIBB in Korea.

As can be seen in Table 17, the result showed that sample treatment group treated with 50, 100, and 500 µg/ml of bamboo extract decreased all the values, TC (Total cholesterol), HDL-C (High-density lipoprotein cholesterol) and TG (Triglycerides) compared with control group in a dose dependent manner.

TABLE 17

| Group | TG | TC | LDL-C | HDL-C |
|---|---|---|---|---|
| NC | 285 ± 119.02 | 3207.5 ± 562.64 | 3125 ± 533.26 | 25 ± 10.00 |
| Lovastatin | 300.00 ± 14.14 | 3750.00 ± 42.43 | 3485.00 ± 304.06 | 25.00 ± 7.07 |

TABLE 17-continued

| Group | TG | TC | LDL-C | HDL-C |
|---|---|---|---|---|
| Bamboo 50 | 313.33 ± 130.51 | 3063.33 ± 166.23 | 2963.33 ± 189.30 | 40.00 ± 26.46 |
| Bamboo 100 | 240.00 ± 36.06 | 3000.67 ± 219.62 | 2903.33 ± 205.02 | 23.33 ± 5.77 |
| Bamboo 500 | 186.67 ± 32.15 | 2930.00 ± 278.39 | 2870.00 ± 278.39 | 23.33 ± 5.77 |

Experimental Example 7

Effect of Bamboo Extract on the Change of Blood Lipid in C57BL/6J Mouse

To investigate the effect of bamboo extract on the change of blood lipid in C57BL/6J mouse, following method was performed.

At the end of experiment, all the mice were anesthetized with 0.12% of avertin and exsanguinations was performed from infraorbitalis plexus venosus with heparin treated capillary. And then blood plasma was isolated by centrifugation at the speed of 11,000 g for 10 minutes and left alone at −70° C. before use. The value of blood lipid was determined by three categories i.e., TC (Total cholesterol), HDL-C (High-density lipoprotein cholesterol) and TG (Triglycerides) at KRIBB in Korea.

As can be seen in Table 18, the result showed that sample treatment group treated with 50, 100 μg/ml of bamboo extract decreased all the values, TC (Total cholesterol), HDL-C (High-density lipoprotein cholesterol) and TG (Triglycerides) compared with control group in a dose dependent manner.

TABLE 18

|  | Total cholesterol | Triglycerides | HDL-C | LDL-C |
|---|---|---|---|---|
| Control | 366.20 ± 71.06 | 73.80 ± 19.52 | 56.00 ± 8.34 | 84.80 ± 20.04 |
| Bamboo 50 | 282.60 ± 35.52 | 64.80 ± 15.55 | 47.40 ± 7.89 | 62.40 ± 8.62 |
| Bamboo 100 | 285.00 ± 12.25 | 52.50 ± 9.26 | 54.25 ± 8.42 | 57.75 ± 2.36 |

Experimental Example 8

Inhibition Effect of Bamboo Extract on Arteriosclerosis in LDL Defected Mouse

To investigate the inhibiting effect of bamboo extract on the occurrence of arteriosclerosis and the progress of the lesion in LDL defected mouse, following method was performed.

At the end of experiment, the exsanguinated heart was fixed with 4% paraformaldehyde dissolved in 0.1M phosphate buffer (pH 7.4) and delivered removing remaining blood and fixing with 10% neutral formalin. And then it is embedded with OCT compound, sliced into 0.6 μm of thickness, stained with oil red O and count-stained with Harris hematoxylin to observe the lesion.

The calculation of lesion area was performed by staining the lesion formed at the position between $3^{rd}$ cervical blood and aortic valve and photocopying and then the lesion area was calculated by using computer-assisted morphometry (TDI microscope Image Analyzer, USA) comparing with control group.

Figure 17:
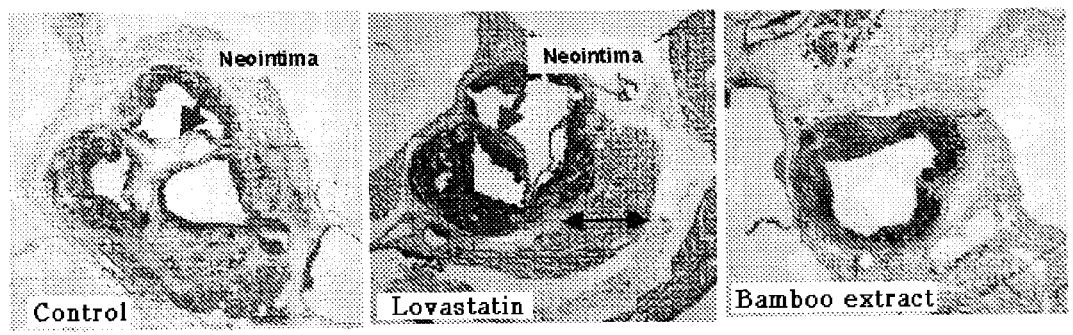
FIGS. 17 and 18 show the morphometry of Oil red O stained aortic valve lesion areas by computer-associated mage analysis in the high cholesterol diet induced atherosclerosis mice with or without the treatment of bamboo extract for 16-weeks (50 and 100 mg/kg) and 20-weeks (500 mg/kg)
Figure 18:
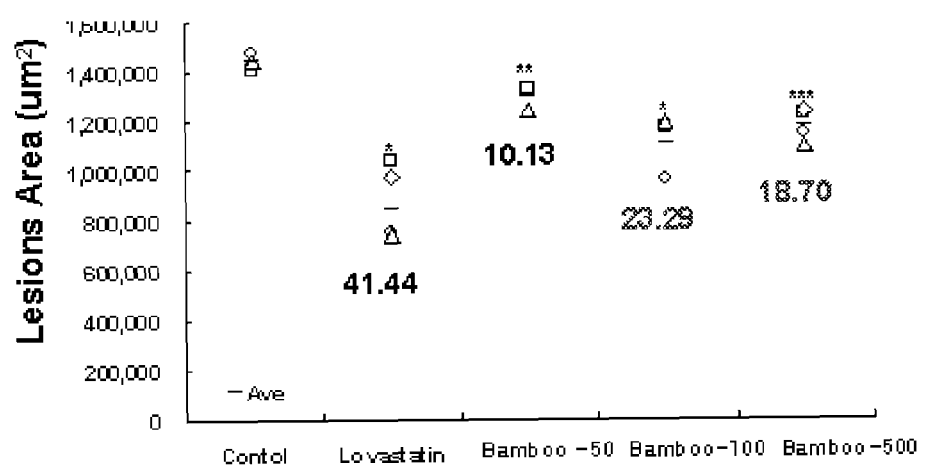

At the result, sample treatment group inhibit the formation of arteriosclerosis by about 17% compared with control group while lovastatin used as a positive control inhibit by about 47% and prevent the formation of neointima (See FIGS. 17 and 18).

Experimental Example 9

Cell Toxicity Test and Cell Proliferation Assay

The cell toxicity of tricin compound of Example 5 was tested using modified MTT method (*J. Immunological Methods*, 119, pp 203-210, 1989).

200 μl of HUVEC ($2 \times 10^5$ cells/ml) on flat bottom 96-well microtiter plates (Nunc, Sweden) were treated with tricin prepared in various concentrations and cultured at 37° C. for 24 hours.

50 μl of MTT solution (1 mg/ml) was added to each well and incubated at 37° C. for 4 hours. And then supernatant was removed.

To detect formazan crystal, 100 μl of DMSO was also added to each well and the colorigenic analysis was performed at 550 nm using microplate reader (Power wave-XS, Bio-Tek, USA).

Figure 5:
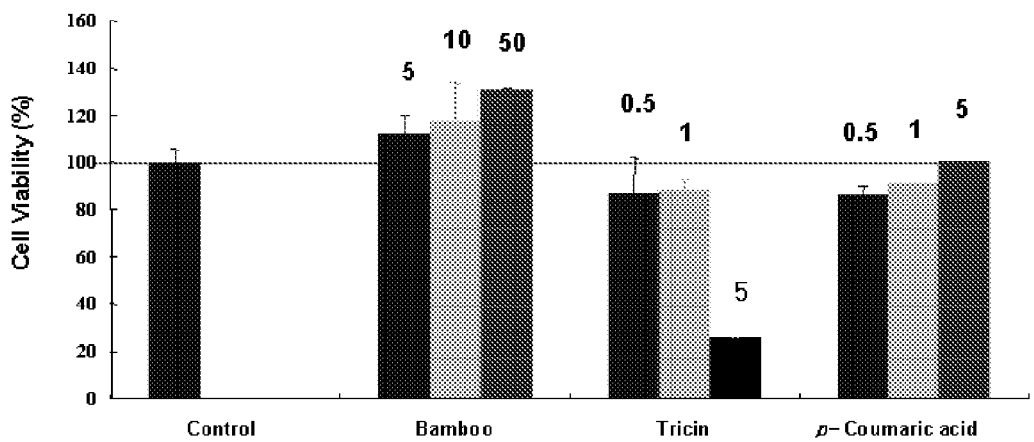
FIG. 5 shows the cellular toxicity of bamboo extract, tricin and p-coumaric acid in the HUVEC, wherein the numbers described above the graph bars denote the concentration of treated sample (μg/ml)

As the result, the inventive tricin compound showed the 51% of strong cellular toxicity at 5 μg/ml, however, bamboo extract or p-coumaric acid was no cellular toxicity (See FIG. 5).

The cell proliferation assay of banjo extract was performed using Cell Proliferation ELISA BrdU colorimetric kit (Roche). HUVEC were seed $5 \times 10^3$ cells/well in 96 well plate. Triplicate plate of cells were measured using ELISA Reader.

Figure 6:
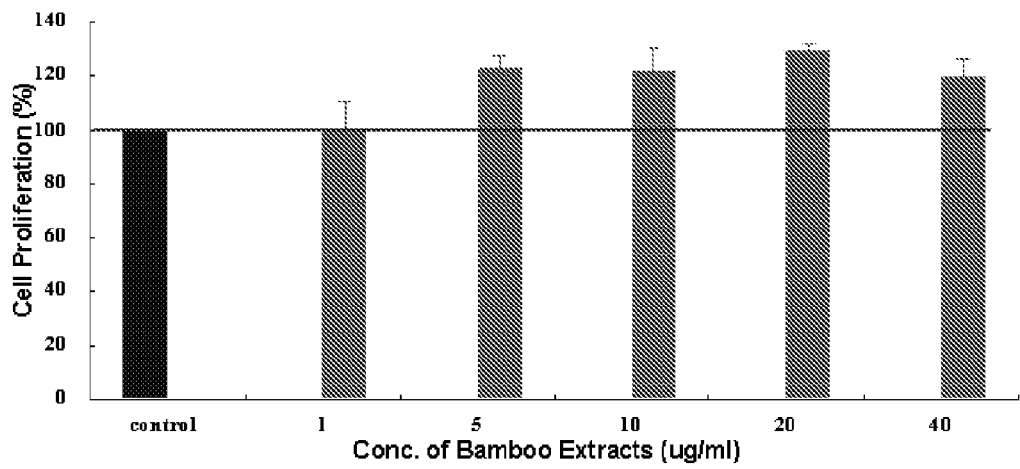
FIG. 6 shows the cell proliferation effect of bamboo extract in the HUVEC.

As the result, bamboo extract enhanced strong cellular proliferation by dose dependent manner (See FIG. 6)

Experimental Example 10

Animal Toxicity Test

Methods (1)

The acute toxicity tests on ICR mice (mean body weight 25±5 g) and Sprague-Dawley rats (235±10 g, Jung-Ang Lab Animal Inc.) were performed using the extract of the Example 1. Four group consisting of 10 mice or rats was administrated orally intraperitoneally with 250 mg/kg, 500 mg/kg, 1000 mg/kg and 5000 mg/kg of test sample or solvents (0.2 ml, i.p.) respectively and observed for 2 weeks.

Methods (2)

The acute toxicity tests on ICR mice and Sprague-Dawley rats were performed using the extract of the Example 1. Four group consisting of 10 mice or rats was administrated intraperitoneally with 25 mg/kg, 250 mg/kg, 500 mg/kg and 725 mg/kg of test sample or solvents (0.2 ml, i.p.), respectively and observed for 24 hours.

Results

There were no treatment-related effects on mortality, clinical signs, body weight changes and gross findings in any group or either gender. These results suggested that the extract prepared in the present invention were potent and safe.

Hereinafter, the formulating methods and kinds of excipients will be described, but the present invention is not limited to them. The representative preparation examples were described as follows.

Preparation of Powder

| | |
|---|---|
| Dried powder of Example 1 | 50 mg |
| Lactose | 100 mg |
| Talc | 10 mg |

Powder preparation was prepared by mixing above components and filling sealed package.

Preparation of Tablet

| | |
|---|---|
| Dried powder of Example 1 | 50 mg |
| Corn Starch | 100 mg |
| Lactose | 100 mg |
| Magnesium Stearate | 2 mg |

Tablet preparation was prepared by mixing above components and entabletting.

Preparation of Capsule

| | |
|---|---|
| Dried powder of Example 1 | 50 mg |
| Corn starch | 100 mg |
| Lactose | 100 mg |
| Magnesium Stearate | 2 mg |

Tablet preparation was prepared by mixing above components and filling gelatin capsule by conventional gelatin preparation method.

Preparation of Injection

| | |
|---|---|
| Dried powder of Example 1 | 50 mg |
| Distilled water for injection | optimum amount |
| PH controller | optimum amount |

Injection preparation was prepared by dissolving active component, controlling pH to about 7.5 and then filling all the components in 2 ml ample and sterilizing by conventional injection preparation method.

Preparation of Liquid

| | |
|---|---|
| Dried powder of Example 1 | 0.1~80 g |
| Sugar | 5~10 g |
| Citric acid | 0.05~0.3% |
| Caramel | 0.005~0.02% |
| Vitamin C | 0.1~1% |
| Distilled water | 79~94% |
| $CO_2$ gas | 0.5~0.82% |

Liquid preparation was prepared by dissolving active component, filling all the components and sterilizing by conventional liquid preparation method.

Preparation of Health Care Food

| | |
|---|---|
| Extract of Example 1 | 1000 mg |
| Vitamin mixture | optimum amount |
| Vitamin A acetate | 70 mg |
| Vitamin E | 1.0 mg |
| Vitamin $B_1$ | 0.13 mg |
| Vitamin $B_2$ | 0.15 mg |
| Vitamin B6 | 0.5 mg |
| Vitamin B12 | 0.2 mg |
| Vitamin C | 10 mg |
| Biotin | 10 mg |
| Amide nicotinic acid | 1.7 mg |
| Folic acid | 50 mg |
| Calcium pantothenic acid | 0.5 mg |
| Mineral mixture | optimum amount |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

The above-mentioned vitamin and mineral mixture may be varied in many ways. Such variations are not to be regarded as a departure from the spirit and scope of the present invention.

Preparation of Health Beverage

| | |
|---|---|
| Extract of Example 1 | 1000 mg |
| Citric acid | 1000 mg |
| Oligosaccharide | 100 g |
| Apricot concentration | 2 g |
| Taurine | 1 g |
| Distilled water | 900 ml |

Health beverage preparation was prepared by dissolving active component, mixing, stirred at 85° C. for 1 hour, filtered and then filling all the components in 1000 ml ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the bamboo plant extract and the tricin compound therefrom have potent anti-inflammatory activity by inhibiting NO production and PLA expression, blood circulation-improving activity by inhibiting elastase activity and healing the wound of vascular endothelial cell, activating u-PA expression and inhibiting PAI-1 expression, lowering cholesterol deposit and inhibiting neointima formation, therefore, it can be used as a therapeutic, health care food for treating and preventing inflammatory or blood circulation diseases.

The invention claimed is:

1. A method for treating a blood circulation disorder selected from the group consisting of arteriosclerosis, thrombosis, and endothelial injury wherein said method comprises administering to a subject in need thereof a therapeutically effective amount of a composition comprising a crude extract or a non-polar solvent soluble extract of Bamboo plant.

2. The method according to claim 1 wherein said crude extract is extracted with a solvent selected from the group consisting of water, lower alcohol and the mixture thereof.

3. The method according to claim 1 wherein said non-polar solvent soluble extract is extracted with non-polar solvent selected from the group consisting of hexane, ethyl acetate, chloroform and dichloromethane.

4. The method according to claim 1 wherein said bamboo is *Sasa* or *Phyllostachys*.

5. The method according to claim 1 wherein said bamboo plant is selected from the group consisting of *Phyllostachys bambusoides* SIEB. Et Zucc, *Phyllostachys nigra* MUNRO, *Phyllostachys nigra* MUNRO var. *henonis* STAPF and *Phyllostachys pubescens* MAZEL ex H. de LEH.

6. The method according to claim 1 wherein said blood circulation disorder is treated by decreasing an elevated lipid component in the circulating blood wherein said elevated lipid component is selected from the group consisting of cholesterol, low density lipoproteins, very low density lipoproteins and triglycerides.

* * * * *